United States Patent
Wellman et al.

(10) Patent No.: US 11,523,839 B2
(45) Date of Patent: Dec. 13, 2022

(54) SYSTEMS AND METHODS FOR GRASP ADJUSTMENT BASED ON GRASP PROPERTIES

(71) Applicant: INTUITIVE SURGICAL OPERATIONS, INC., Sunnyvale, CA (US)

(72) Inventors: Ashley Lynne Wellman, East Palo Alto, CA (US); David W. Weir, San Carlos, CA (US); Matthew A. Wixey, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 906 days.

(21) Appl. No.: 16/366,854

(22) Filed: Mar. 27, 2019

(65) Prior Publication Data
US 2019/0298398 A1 Oct. 3, 2019

Related U.S. Application Data

(60) Provisional application No. 62/652,040, filed on Apr. 3, 2018.

(51) Int. Cl.
*A61B 34/00* (2016.01)
*A61B 34/30* (2016.01)
(Continued)

(52) U.S. Cl.
CPC ...... *A61B 17/282* (2013.01); *A61B 17/22031* (2013.01); *A61B 34/35* (2016.02);
(Continued)

(58) Field of Classification Search
CPC . A61B 17/282; A61B 17/22031; A61B 34/35; A61B 34/76; A61B 34/25;
(Continued)

(56) References Cited

U.S. PATENT DOCUMENTS

| 4,957,320 A | * | 9/1990 | Ulrich | B25J 15/0009 294/111 |
| 5,103,404 A | * | 4/1992 | McIntosh | G05B 19/4142 318/568.22 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jaime Figueroa
(74) *Attorney, Agent, or Firm* — Artegis Law Group, LLP

(57) ABSTRACT

Systems and methods for grasp adjustment based on grasp properties include a computer-assisted device. The device includes a two-jawed end effector located at a distal end of the device, a drive unit for operating the two-jawed end effector, and an image processing unit. The image processing unit is configured to receive imaging data of the end effector and recognize the end effector and a material grasped by the end effector in the received imaging data. The device is configured to adjust a force magnitude limit or a torque magnitude limit of the drive unit based on the received imaging data. In some embodiments, the image processing unit is further configured to determine one or more of a position, an orientation, a size, or a shape of the material based on the received imaging data. In some embodiments, at least one jaw of the end effector includes fiducial indicia.

20 Claims, 7 Drawing Sheets

(51) Int. Cl.
    *A61B 17/28*           (2006.01)
    *A61B 17/22*           (2006.01)
    *A61B 34/35*           (2016.01)
    *A61B 34/20*           (2016.01)
    *A61B 90/00*           (2016.01)

(52) U.S. Cl.
    CPC .............. *A61B 34/76* (2016.02); *A61B 34/25* (2016.02); *A61B 34/77* (2016.02); *A61B 90/37* (2016.02); *A61B 2034/2065* (2016.02); *A61B 2034/305* (2016.02)

(58) Field of Classification Search
    CPC . A61B 34/77; A61B 90/37; A61B 2034/2065; A61B 2034/305; A61B 2090/064
    USPC ................. 700/245–264; 318/568.11–568.25
    See application file for complete search history.

(56) References Cited

U.S. PATENT DOCUMENTS

| | | | | |
|---|---|---|---|---|
| 5,734,373 | A * | 3/1998 | Rosenberg | A63F 13/285 345/161 |
| 6,219,033 | B1 * | 4/2001 | Rosenberg | G06F 3/011 345/157 |
| 6,377,011 | B1 * | 4/2002 | Ben-Ur | G06F 3/016 345/184 |
| 6,419,626 | B1 * | 7/2002 | Yoon | A61B 1/00052 600/117 |
| 9,014,856 | B2 * | 4/2015 | Manzo | A61B 34/37 901/19 |
| 9,447,532 | B2 * | 9/2016 | Jurkovic | D05B 19/12 |
| 10,232,194 | B2 * | 3/2019 | Schlosser | A61N 5/1039 |
| 10,357,270 | B2 * | 7/2019 | Overmyer | A61B 17/295 |
| 10,702,349 | B2 * | 7/2020 | Overmyer | A61B 17/07207 |
| 2001/0030658 | A1 * | 10/2001 | Rosenberg | G01B 21/04 715/701 |
| 2006/0020213 | A1 * | 1/2006 | Whitman | A61B 1/05 600/478 |
| 2006/0142897 | A1 * | 6/2006 | Green | B25J 3/04 348/E13.016 |
| 2007/0151389 | A1 * | 7/2007 | Prisco | B25J 9/1633 74/490.05 |
| 2008/0046122 | A1 * | 2/2008 | Manzo | A61B 90/98 700/245 |
| 2009/0012538 | A1 * | 1/2009 | Saliman | A61B 17/0491 606/228 |
| 2009/0067973 | A1 * | 3/2009 | Eliuk | B66C 1/42 700/231 |
| 2009/0182193 | A1 * | 7/2009 | Whitman | A61B 1/00133 600/104 |
| 2011/0015649 | A1 * | 1/2011 | Anvari | A61B 34/20 606/130 |
| 2011/0066160 | A1 * | 3/2011 | Simaan | A61N 1/05 606/129 |
| 2011/0087246 | A1 * | 4/2011 | Saliman | A61B 17/0491 606/145 |
| 2013/0038707 | A1 * | 2/2013 | Cunningham | A61B 1/00009 382/131 |
| 2013/0066332 | A1 * | 3/2013 | Sutherland | A61B 34/30 606/1 |
| 2013/0110130 | A1 * | 5/2013 | Manzo | A61B 34/71 606/130 |
| 2015/0201711 | A1 * | 7/2015 | Jurkovic | A43B 23/025 12/142 R |
| 2015/0209599 | A1 * | 7/2015 | Schlosser | A61B 8/085 600/427 |
| 2015/0305715 | A1 * | 10/2015 | Tan | G01S 7/52077 600/443 |
| 2017/0000218 | A1 * | 1/2017 | Jurkovic | A43B 23/025 |
| 2017/0173795 | A1 * | 6/2017 | Tan | B25J 9/1664 |
| 2018/0214168 | A1 * | 8/2018 | Overmyer | A61B 17/295 |
| 2018/0338803 | A1 * | 11/2018 | Meglan | A61B 1/00137 |
| 2019/0059890 | A1 * | 2/2019 | Shelton, IV | A61B 17/295 |
| 2019/0059891 | A1 * | 2/2019 | Shelton, IV | A61B 17/07207 |
| 2019/0099180 | A1 * | 4/2019 | Leimbach | G16H 40/63 |
| 2019/0142420 | A1 * | 5/2019 | Collings | A61B 17/07207 227/175.1 |
| 2019/0201104 | A1 * | 7/2019 | Shelton, IV | A61B 1/00011 |
| 2019/0254762 | A1 * | 8/2019 | Overmyer | A61B 34/37 |

* cited by examiner

SYSTEMS AND METHODS FOR GRASP ADJUSTMENT BASED ON GRASP PROPERTIES

RELATED APPLICATIONS

This application claims priority to U.S. Provisional Patent Application No. 62/652,040 (filed Apr. 3, 2018), which is incorporated herein by reference.

TECHNICAL FIELD

The present disclosure relates generally to operation of devices with articulated arms and end effectors and more particularly to force or torque adjustment based on grasp properties.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held instruments are being replaced by computer-assisted devices.

Minimally invasive surgical techniques using computer-assisted devices generally attempt to perform surgical and/or other procedures while minimizing damage to healthy tissue. Some minimally invasive procedures may be performed remotely through the use of computer-assisted devices with instruments. With many computer-assisted devices, an operator may typically manipulate input devices using one or more controls on an operator console. As the operator operate the various controls at the operator console, the commands are relayed from the operator console to a patient side device to which one or more end effectors and/or instruments are mounted. In this way, the operator are able to perform one or more procedures on a patient using the end effectors and/or instruments. Depending upon the desired procedure and/or the instruments in use, the desired procedure may be performed partially or wholly under control of the operator using teleoperation and/or under semi-autonomous control where the instrument may perform a sequence of operations based on one or more activation actions by the operator.

Minimally invasive instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thorascopically, and/or the like) through an opening (e.g., a body wall incision, a natural orifice, and/or the like) to reach a remote worksite of interest. In some instruments, an articulating wrist mechanism may be mounted to the distal end of the instrument's shaft to support the end effector with the articulating wrist, providing the ability to alter an orientation of the end effector relative to a longitudinal axis of the shaft.

End effectors of different design and/or configuration may be used to perform different tasks, procedures, and functions so as to allow the operator to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept as small as possible while still allowing it to perform its intended task. One approach to keeping the size of the end effector small is to accomplish actuation of the end effector through the use of one or more inputs at a proximal end of the instrument, which is typically located externally to the patient. Various gears, levers, pulleys, cables, rods, bands, and/or the like, may then be used to transmit actions from the one or more inputs along the shaft of the instrument and to actuate the end effector. In the case of a computer-assisted device with an appropriate instrument, a transmission mechanism at the proximal end of the instrument interfaces with various motors, solenoids, servos, active actuators, hydraulics, pneumatics, and/or the like provided on an articulated arm of the patient side device or a patient side cart. The motors, solenoids, servos, active actuators, hydraulics, pneumatics, and/or the like typically receive control signals through a master controller and provide input in the form of force and/or torque at the proximal end of the transmission mechanism, which the various gears, levers, pulleys, cables, rods, bands, and/or the like ultimately transmit to actuate the end effector at the distal end of the transmission mechanism.

It is often desirable to use the end effectors for grasping a material such as tissue. In some examples, when the end effectors grasp the material, some other operation such as stapling or cutting may be performed on the grasped material. However, grasp performance is often affected by the type and amount of material being grasped, the shape of the material being grasped, the position of the material within the jaws of the end effector, and/or the like. Accordingly, improved methods and systems for controlling the grasping operation of the end effectors is desirable.

SUMMARY

Consistent with some embodiments, a computer-assisted device includes a two-jawed end effector located at a distal end of the device, a drive unit for operating the two-jawed end effector, and an image processing unit. The image processing unit is configured to receive imaging data of the two-jawed end effector and recognize the two-jawed end effector and a material grasped by the two-jawed end effector in the received imaging data. The device is configured to adjust a force magnitude limit or a torque magnitude limit of the drive unit based on the received imaging data.

Consistent with some embodiments, a method of operating a computer-assisted device includes receiving, by an image processing unit executing on one or more processors, imaging data of a two-jawed end effector, recognizing the two-jawed end effector and a material grasped by the two-jawed end effector in the received imaging data, determining a position, an orientation, a size, or a shape of the material relative to the two-jawed end effector, determining whether the position, the size or the shape is determined with confidence, and adjusting, when the position, the orientation, the size, or the shape determination is with confidence, a force magnitude limit or a torque magnitude limit to the two-jawed end effector or applying, when the position determination is without confidence, a default force magnitude limit or a default torque magnitude limit to the two-jawed end effector.

Consistent with some embodiments, a non-transitory machine-readable medium having stored thereon machine-readable instructions executable to cause a machine to perform any of the methods disclosed herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
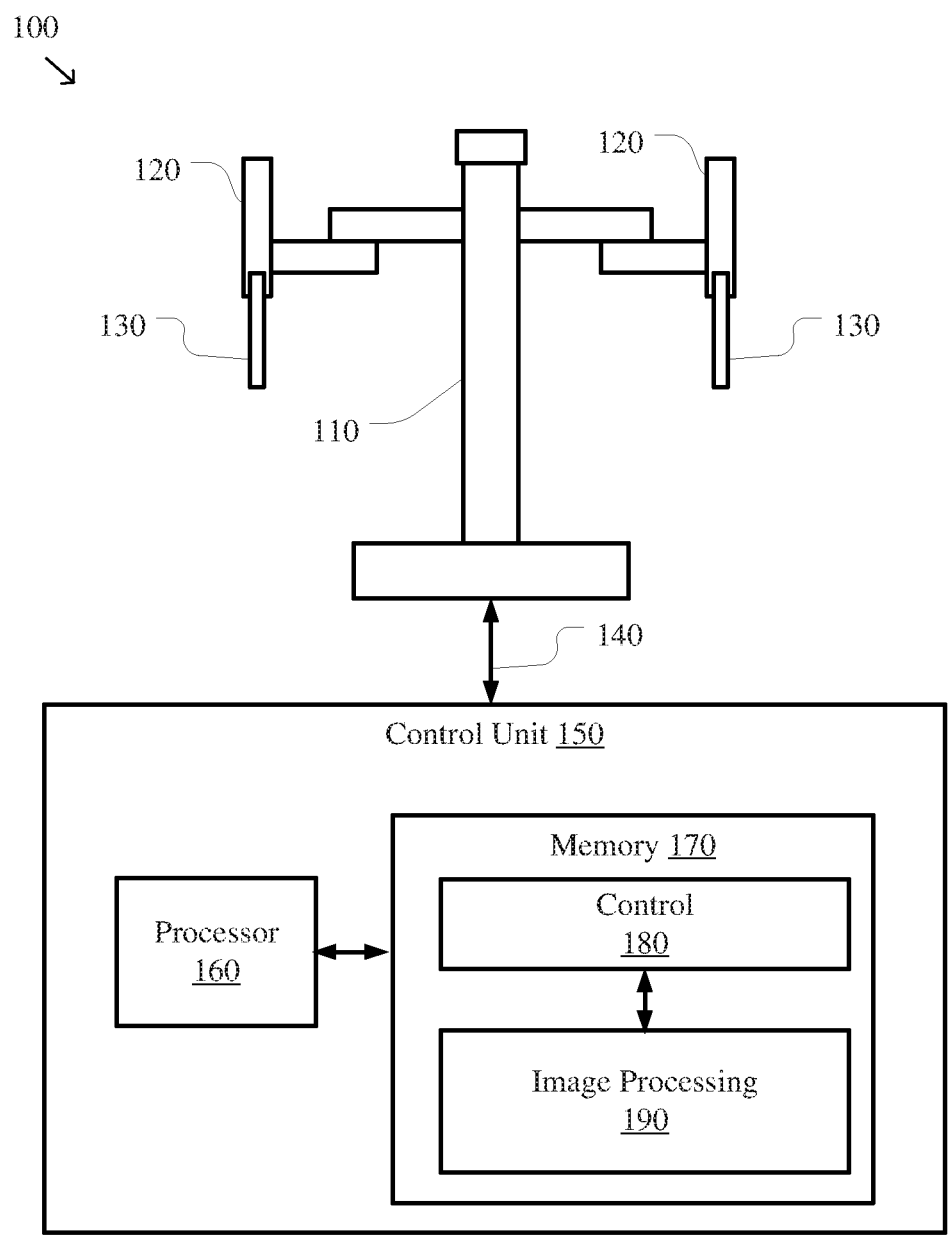
FIG. 1 is a simplified diagram of a computer-assisted system, according to some embodiments.

In the figures, elements having the same designations have the same or similar functions.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, components, methods, procedures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

This disclosure describes various instruments, portions of instruments, materials (e.g., tissues), and/or the like in terms of their state in three-dimensional space. As used herein, the term "position" refers to the position and/or location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "proximal" refers to a direction toward a base of a device with repositionable arms and "distal" refers to a direction away from the base.

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

In some embodiments the magnitude of a force and/or a torque may be limited to stay under a certain threshold that is determined based on development experiments and is adjusted using available real-time information, such as in-cannula compensation to adjust for friction variations. In some examples, a higher force and/or torque magnitude limit may be set if full insertion of the material may be assumed, and a lower force and/or torque magnitude limit may be set if the material is assumed to be partially inserted into the jaws. If the torque is set based on the full insertion values, the force and/or torque magnitude limit may allow a higher force and/or torque magnitude than it may be allowed for partial insertion, resulting in excessive tip deflection. If the force and/or torque magnitude limit is set based on the partial material insertion, the force and/or torque magnitude limit will be set lower, and at full insertion, the operator of the instrument may not be able to achieve full grasp on target material. Thus, the ability to know how far the material is inserted between the jaws, how much material is inserted between the jaws, a shape, an orientation, and/or a size of the material between the jaws, one or more material properties of the material, and/or the like would allow the software to adjust the force and/or torque magnitude limit at the point-of-use based on the material observations.

FIG. 1 is a simplified diagram of a computer-assisted system 100 according to some embodiments. As shown in FIG. 1, computer-assisted system 100 includes a computer-assisted device 110, e.g., computer-assisted device, with one or more movable or articulated arms 120. Each of the one or more articulated arms 120 may support one or more instruments, e.g., instruments 130. In some examples, computer-assisted device 110 may be consistent with a computer-assisted surgical device. The one or more articulated arms 120 may each provide support for instruments 130 such as, imaging devices, and/or the like. In some examples, the instruments 130 may include end effectors that are capable of, but are not limited to, performing, grasping, retracting, cauterizing, ablating, suturing, cutting, stapling, fusing, sealing, etc., and/or combinations thereof. In some examples, an imaging device may include an endoscopic camera.

Computer-assisted device 110 may further be coupled to an operator workstation (not shown), which may include one or more master controls for operating the computer-assisted device 110, the one or more articulated arms 120, and/or the instruments 130. In some examples, the one or more master controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with computer-assisted system 100.

Computer-assisted device 110 is coupled to a control unit 150 via an interface 140. The interface 140 may include one or more cables, fibers, connectors, and/or buses and may further include one or more networks with one or more network switching and/or routing devices. Control unit 150 includes a processor 160 coupled to memory 170. Operation of control unit 150 may be controlled by processor 160. And although control unit 150 is shown with only one processor 160, it is understood that processor 160 may be representative of one or more central processing units, multi-core processors, microprocessors, microcontrollers, digital signal processors, graphics processing units, field programmable gate arrays (FPGAs), application specific integrated circuits (ASICs), and/or the like in control unit 150. Control unit 150 may be implemented as a stand-alone subsystem and/or board added to a computing device or as a virtual machine. In some embodiments, control unit 150 may be included as part of the operator workstation and/or operated separately from, but in coordination with the operator workstation.

Memory 170 may be used to store software executed by control unit 150 and/or may include one or more data structures used during operation of control unit 150. Memory 170 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 170 may include a control module 180 that may be used to support autonomous, semiautonomous, and/or teleoperated control of computer-assisted device 110. Control module 180 may include one or more application programming interfaces (APIs) for receiving position, motion, force, torque, and/or other sensor information from computer-assisted device 110, articulated arms 120, and/or instruments 130, exchanging position, motion, force, torque, and/or collision avoidance information with other control units regarding other devices, and/or planning and/or assisting in the planning of motion for computer-assisted device 110, articulated arms 120, and/or instruments 130. The control module 180 may receive the sensor information from computer-assisted device 110 through interface 140 and control unit 150 and may communicate control signals through interface 140 and control unit 150 to computer-assisted device 110. In some examples, control module 180 may further support autonomous, semi-autonomous, and/or teleoperated control of the instruments 130 during a surgical procedure. And although control module 180 is depicted as a software application that may be executed on processor 160, control module 180 may be implemented using standalone hardware separate from the processor 160 or may be implemented as a combination of the standalone hardware and software executed on processor 160.

As further shown in FIG. 1, memory 170 may include an image processing module 190 that may be used to support image processing tasks related to one or more materials being manipulated by computer-assisted device 110 and/or an environment in which computer-assisted device 110 is being operated. Image processing module 190 may include one or more application programming interfaces (APIs) for receiving imaging data that comprises one or more digital images. The imaging data may be received, through interface 140 and control unit 150, from an articulated arm 120 that includes an imaging device. Image processing module 190 may recognize one or more objects in the imaging data and may communicate dimensions, positions, shapes, sizes, material properties, scores (e.g., confidence factors, of the recognized objects), and/or the like to the control module 180. And although image processing module 190 is depicted as a software application that may be executed on processor 160, image processing module 190 may be implemented using standalone hardware separate from the processor 160 or may be implemented as a combination of the standalone hardware and software executed on processor 160.

In some embodiments, computer-assisted system 100 may be found in an operating room and/or an interventional suite. And although computer-assisted system 100 includes only one computer-assisted device 110 with two articulated arms 120 and corresponding instruments 130, one of ordinary skill would understand that computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

In some embodiments, the imaging data may be received by the control unit 150 from an imaging device of an articulated arm 120 of another computer-assisted device different from the computer-assisted device 110.

Figure 2:
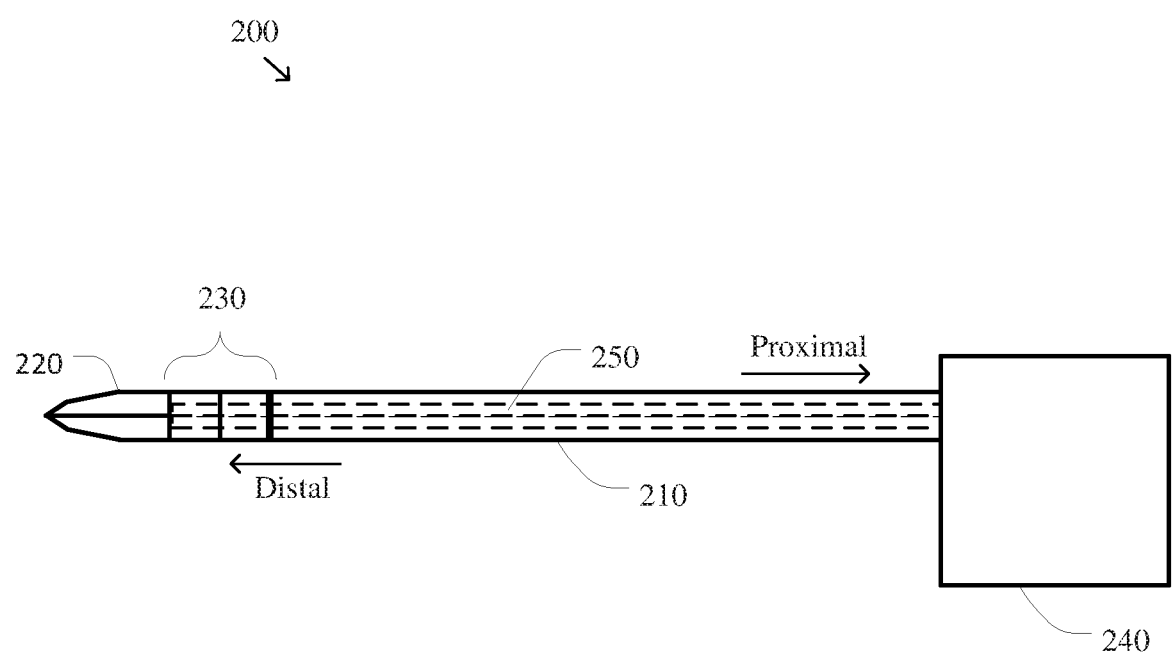
FIG. 2 is a simplified diagram showing an instrument, according to some embodiments.

FIG. 2 is a simplified diagram showing an instrument 200 according to some embodiments. In some embodiments, instrument 200 may be consistent with any of the instruments 130 of FIG. 1. The directions "proximal" and "distal" as depicted in FIG. 2 and as used herein help describe the relative orientation and position of components of instrument 200. Distal generally refers to elements in a direction further along a kinematic chain from a base of a computer-assisted device, such as computer-assisted device 110, and/or or closest to the worksite in the intended operational use of the instrument 200. Proximal generally refers to elements in a direction closer along a kinematic chain toward the base of the computer-assisted device and/or one of the articulated arms of the computer-assisted device.

As shown in FIG. 2, instrument 200 includes a long shaft 210 used to couple an end effector 220, located at a distal end of shaft 210, to where the instrument 200 is mounted to an articulated arm and/or a computer-assisted device at a proximal end of shaft 210. Depending upon the particular procedure for which the instrument 200 is being used, shaft 210 may be inserted through an opening (e.g., a body wall incision, a natural orifice, and/or the like) in order to place end effector 220 in proximity to a worksite of interest located within a work area and/or an object of interest. As further shown in FIG. 2, end effector 220 is generally consistent with a two-jawed gripper-style end effector, which in some embodiments may further include a cutting and/or a fusing or sealing mechanism as is described in further detail below with respect to FIG. 3. However, one of ordinary skill would understand that different instruments 200 with different end effectors 220 are possible and may be consistent with the embodiments of instrument 200 as described elsewhere herein.

A instrument, such as instrument 200 with end effector 220 typically relies on multiple degrees of freedom (DOFs) during its operation. Depending upon the configuration of instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within a worksite that end effector 220 is placed. In some examples, shaft 210 may be able to rotate about its longitudinal axis to provide a roll DOF that may be used to rotate end effector 220. In some examples, additional flexibility in the position and/or orientation of end effector 220 may be provided by an articulated wrist 230 that is used to couple the end effector 220 to the distal end of shaft 210. In some examples, articulated wrist 230 may include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 may further include a grasp DOF used to control the opening, closing, and the torque applied by the jaws of end effector 220.

Instrument 200 further includes a drive system 240 located at the proximal end of shaft 210. Drive system 240 includes one or more components for introducing forces and/or torques to instrument 200 that may be used to manipulate the various DOFs supported by instrument 200. In some examples, drive system 240 may include one or more motors, solenoids, servos, active actuators, hydraulic actuators, pneumatic actuators, and/or the like that are operated based on signals received from a control unit, such as control unit 150 of FIG. 1. In some examples, the signals may include one or more currents, voltages, pulse-width modulated wave forms, and/or the like. In some examples, drive system 240 may include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which instrument 200 is mounted. In some examples, the one or more drive inputs, such as shafts, gears, pulleys, rods, bands, and/or the like, may be used to receive forces and/or torques from the motors, solenoids, servos, active actuators, hydraulics, pneumatics, and/or the like and apply those forces and/or torques to adjust the various DOFs of instrument 200.

In some embodiments, the forces and/or torques generated by and/or received by drive system 240 may be transferred from drive system 240 and along shaft 210 to the various joints and/or elements of instrument 200 located distal to drive system 240 using one or more drive mechanisms 250. In some examples, the one or more drive mechanisms 250 may include one or more gears, levers, pulleys, cables, rods, bands, and/or the like. In some examples, shaft 210 is hollow and the drive mechanisms 250 pass along the inside of shaft 210 from drive system 240 to the corresponding DOF in end effector 220 and/or articulated wrist 230. In some examples, each of the drive mechanisms 250 may be a cable disposed inside a hollow sheath or lumen in a Bowden cable like configuration. In some examples, the cable and/or the inside of the lumen may be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one of the DOFs of end effector 220, articulated wrist 230, and/or instrument 200.

Figure 3:
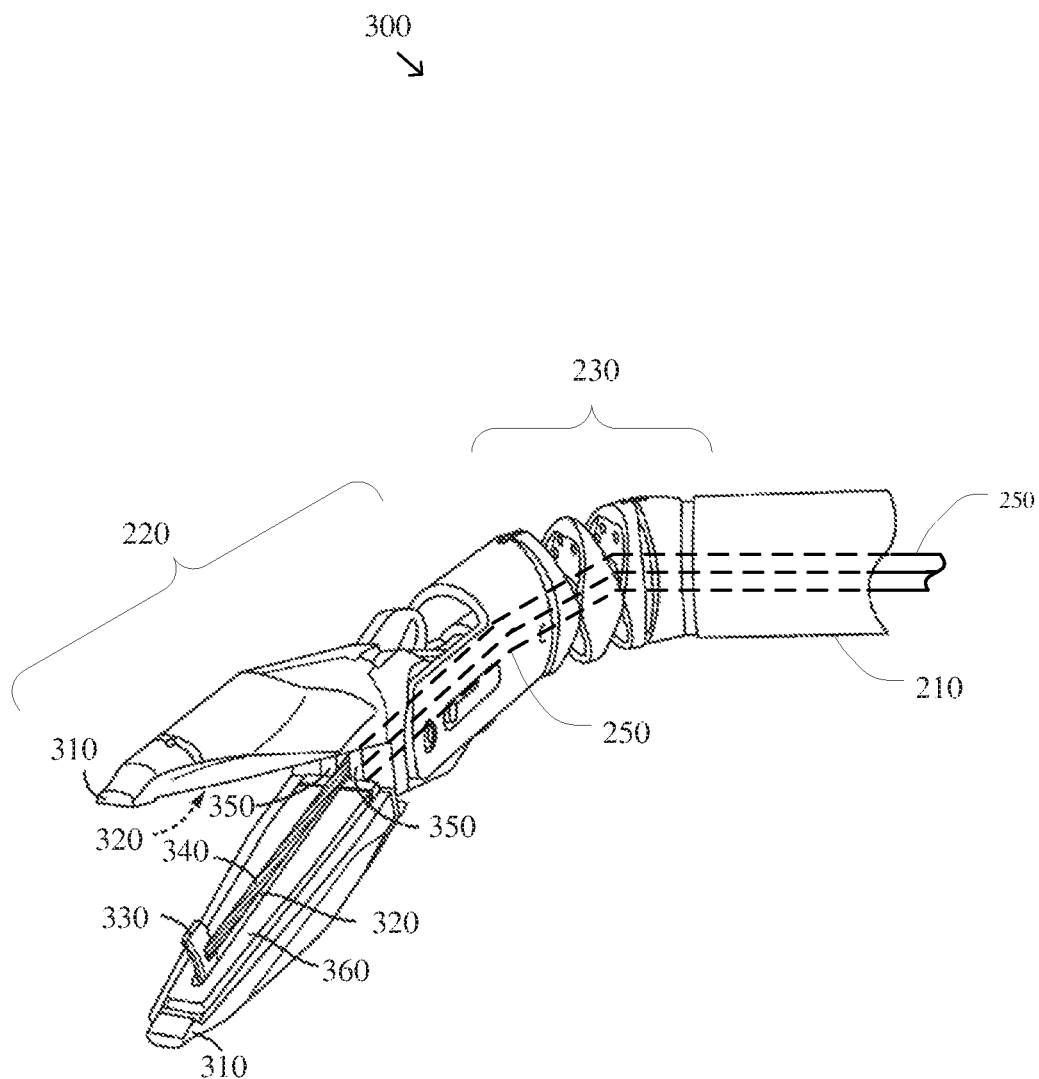
FIG. 3 is a simplified perspective diagram of the distal end of the end effector of FIG. 2, according to some embodiments.

FIG. 3 is a simplified perspective diagram 300 of the distal end of instrument 200 according to some embodiments. As shown in FIG. 3, the distal end of instrument 200 is depicted so as to show additional details of end effector 220, articulated wrist 230, and drive mechanisms 250. In more detail, end effector 220 includes opposing jaws 310 shown in an open position. Jaws 310 are configured to move between open and closed positions so that end effector 220 may be used during a procedure to grasp and release a material such as tissue and/or other structures, such as sutures, located at the worksite of interest (e.g., a surgical site). In some examples, jaws 310 may be operated together as a single unit with both jaws 310 opening and/or closing at the same time. In some examples, jaws 310 may be opened and/or closed independently so that, for example, one jaw 310 could be held steady which the other jaw 310 may be opened and/or closed.

Figure 4:
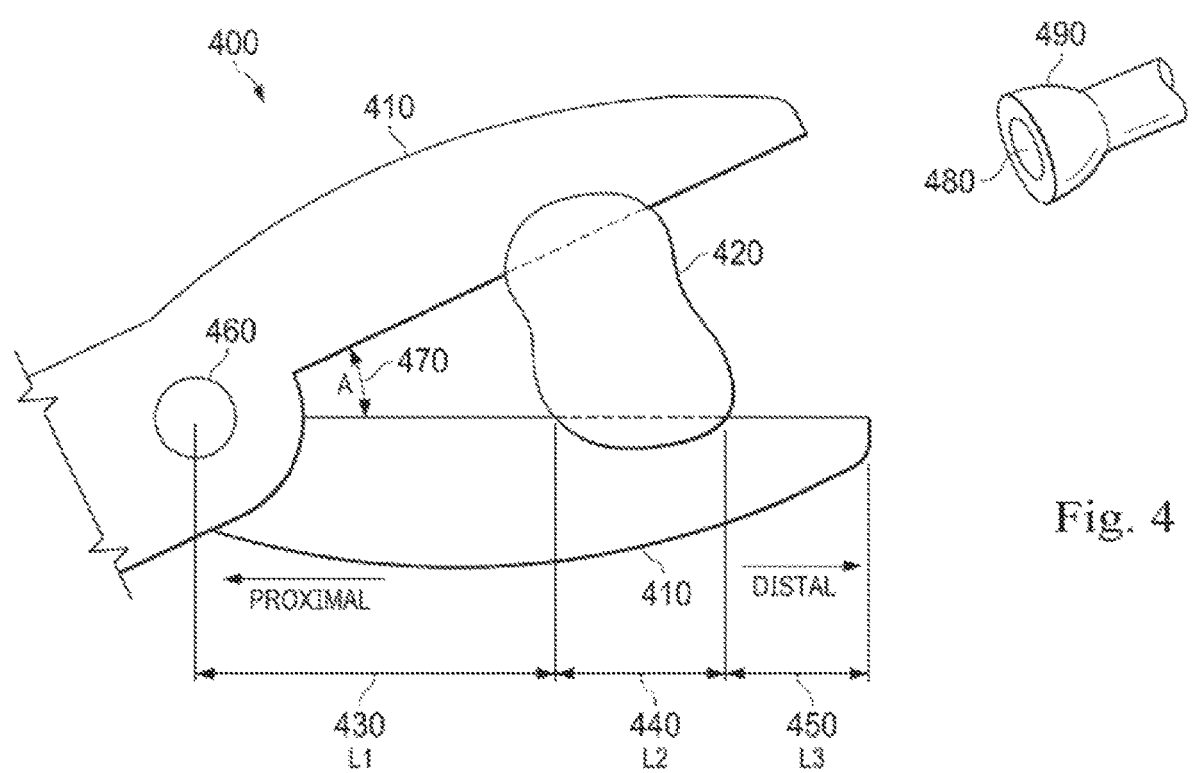
FIG. 4 is a simplified perspective diagram that includes an imaging device as well as a worksite showing the distal end of an end effector grasping a material, according to some embodiments.
Figure 5A:
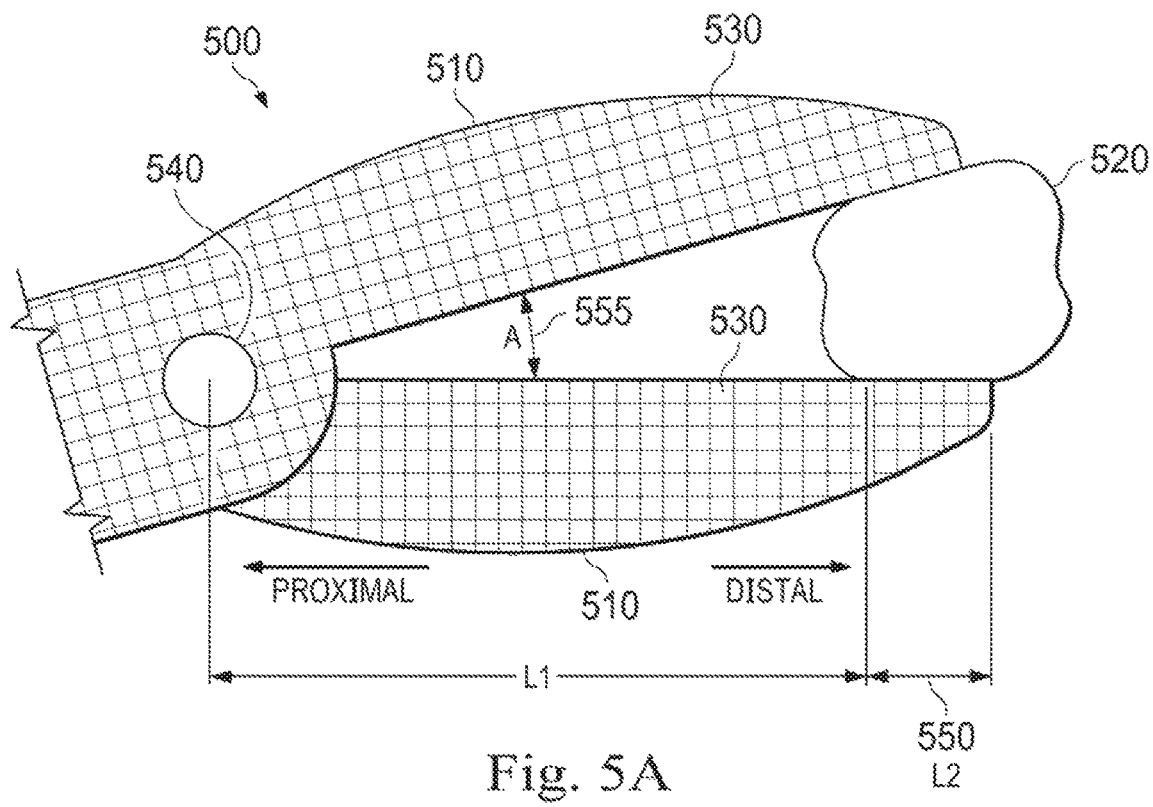
FIGS. 5A-5B are simplified diagrams of the distal end of an end effector grasping a material, according to some embodiments.
Figure 5B:
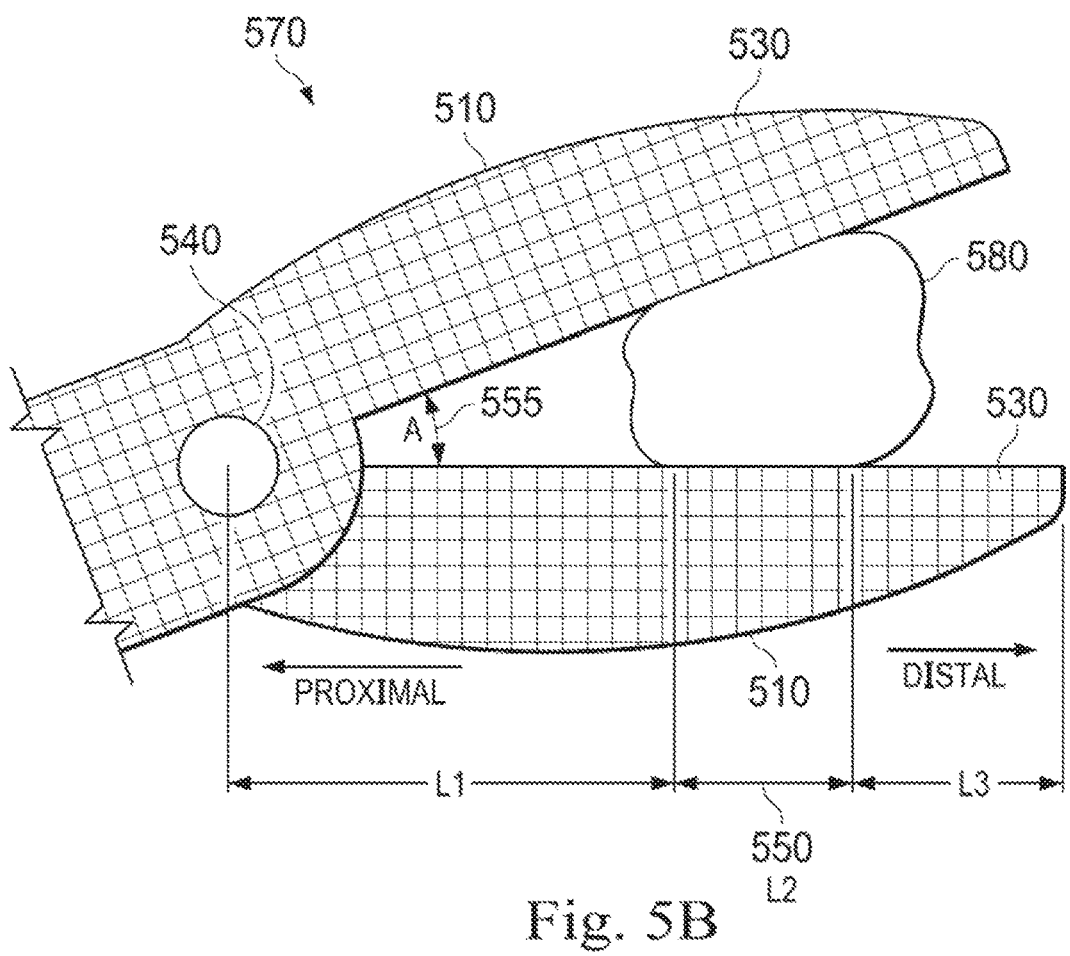

FIG. 3 shows that a grasping surface on an inside of each of jaws 310 includes a corresponding groove 320, which may act as a guide for a cutting blade 330. In some examples, the groove 320 may be omitted from one or both jaws 310. As cutting blade 330 is extended toward the distal end of end effector 220 and/or retracted toward the proximal end of end effector 220, each of the grooves 320 may aid in the alignment and/or positioning of cutting blade 330 during a cutting operation. Extraction and/or retraction of cutting blade 330 is accomplished using a drive component 340 to which cutting blade 330 is attached. In some examples, drive component 340 pushes on cutting blade 330 to extend cutting blade 330 and pulls on cutting blade 330 to retract cutting blade 330. Positioning of the material between the jaws is shown in FIGS. 4, 5A, and 5B, which include simplified cut-away diagrams of the jaws 310 according to some embodiments.

End effector 220 further includes a garage feature 350 located at a proximal end of jaws 310. Garage feature 350 includes an opening through which both drive component 340 and cutting blade 330 may pass. Garage feature 350 is configured to provide a safe storage area for cutting blade 330 when cutting blade 330 is not in use. Thus, when cutting blade 330 is not actively being used as part of a cutting operation, end effector 220 is configured so that cutting blade 330 may be retracted into garage feature 350 in a "garaged" or stored position.

In some embodiments as shown in FIG. 3, the grasping surface on the inside of each of jaws 310 may further include one or more optional electrodes 360. In some examples, electrodes 360 may be used to deliver electrosurgical energy to fuse the material being held between jaws 310. In some examples, electrodes 360 may provide an electro-cautery, fusing, and/or sealing feature to end effector 220 so that the material may be cut and/or fused/sealed using the same instrument 200.

In some embodiments, operation of jaws 310, cutting blade 330, and/or the joints of articulated wrist 230 may be accomplished using corresponding ones of the drive mechanisms 250. In some examples, when jaws 310 are operated independently, a distal end of two of the drive mechanisms 250 (one for each of jaws 310) may be coupled to a respective jaw 310 so that as the corresponding drive mechanism 250 applies a pull and/or a pushing force (for example, using a cable, lead screw, and/or the like), the respective jaw 310 may be opened and/or closed. In some examples, when jaws 310 are operated together, both jaws 310 may be coupled to the distal end of the same drive mechanism 250. In some examples, drive component 340 may be coupled to a distal end of a corresponding drive mechanism 250 so that forces and/or torques applied to the corresponding drive mechanism 250 may be transferred to the push and/or pull motion of drive component 340. In some examples, additional drive mechanisms 250 may be used to operate the roll, pitch, and/or yaw in articulated wrist 230.

FIG. 4 is a simplified perspective diagram that includes an imaging device 490 as well as a worksite 400 showing, at the distal end of an instrument, an end effector grasping a material 420, according to some embodiments. The end effector includes jaws 410, which may be consistent with the jaws of two-jawed gripper-style end effector 220 of FIG. 2 and/or the jaws 310 of FIG. 3. In some embodiments, a material 420 such as tissue may be grasped between jaws 410, which may be operated by drive mechanisms, such as drive mechanisms 250 of FIGS. 2 and 3, to exert force and/or torque to material 420. Referring back to FIG. 1, the jaws 410 may be part of the instrument 130 of the computer-assisted device 110 and the computer-assisted device 110 may be in communication with the control unit 150 and may receive control signals through interface 140 from the control module 180 of control unit 150.

Also shown in FIG. 4 is an imaging device 490 that includes one or more lenses 480 that may be used to capture imaging data of worksite 400. In some examples, imaging device 490 may be an endoscope. Referring back to FIG. 1, the imaging device 490 may be mounted to an articulated arm 120 of the computer-assisted device 110. In some embodiments, the jaws 410 may be mounted to a first articulated arm 120 of the computer-assisted device 110 and the imaging device 490 may be mounted to a second articulated arm 120 of the computer-assisted device 110 and both articulated arms 120 may be coupled through the interface 140 to control unit 150. In some examples, control unit 150 may receive imaging data that is acquired by the imaging device 490. In some embodiments, the imaging device 490 may have more than one lens, for example imaging device 490 may have two or more lenses and is able to generate multiple views of the worksite of interest, including stereoscopic views.

In some embodiments, imaging data of a worksite, e.g., worksite 400, may be acquired by an imaging device consistent with imaging device 490 of FIG. 4. The received imaging data may be transferred through the interface 140 to the control unit 150 for processing by one or more modules of the control unit 150, such as image processing module 190.

As further shown in FIG. 4, a grasping zone 440 within the a jaw may indicate where the jaw 410 and the material 420 are in contact. Also as shown, a length 430 may indicate a length between a proximal end 460 of the jaws 410 where the jaws pivot relative to each other and a proximal end of the grasping zone 440. In some embodiments, an angle 470 between the jaws 410 may be determined. Additionally, a length 450 may indicate a length between a distal end of the grasping zone 440 to the distal end of the jaws 410. In some examples, the length 430 may be referenced as "L1", a grasping length of the grasping zone 440 which is a length of contact between the material and the jaw may be referenced as "L2", and the length 450 may be referenced as "L3" such that a sum of L1, L2, and L3 may equal a length of the jaw 410, which may be a constant. In some embodiments, the material may be grasped at the distal end of the jaw and the length L3 may be zero. In some examples, the angle 470 at the proximal end 460 may be a grasping angle "A"

between the jaws 410. In some examples, the angle A may depend on a size, an orientation, and/or a shape of the material 420 and/or on a position where the material 420 is grasped by the jaws 410.

FIGS. 5A-5B are simplified diagrams of the distal end of an instrument grasping a material according to some embodiments. In some examples, FIGS. 5A and 5B comprise imaging data 500 and 570 captured via an imaging device such as the imaging device 490 of FIG. 4. As shown in FIG. 5A, a material 520, such as tissue, may be grasped by the jaws 510 toward the distal end of the jaws 510. As further shown in FIG. 5A, a grasping zone 550 at a distal end of a jaw may indicate where the jaw 510 and the material 520 are in contact. Additionally, a length L1 indicates a distance between a proximal end 540 of the jaws 510 and a proximal end of the grasping zone 550.

Similarly, as shown in imaging data 570 of FIG. 5B, a material 580, which may be similar to the material 520, may be grasped by the jaws 510. As further shown in FIG. 5B, a grasping zone 550 may indicate where the jaws 510 and the material 580 are in contact. Again, a length L1 indicates a distance between the proximal end 540 of the jaws and a proximal end of the grasping zone 550. Additionally, a length L3 indicates a distance between a distal end of the grasping zone 550 and a distal end of the jaw 510. As shown in FIG. 5B, the grasping zone 550 is in between the length L1 and L3. Also, the length L1 in FIG. 5A may be greater than the length L1 in FIG. 5B and the angle A between the jaws 510 in FIG. 5A may be smaller than the angle A between the jaws 510 in FIG. 5B even when the material 520 and 580 have substantially the same size and/or shape.

As further shown in FIGS. 5A and 5B, fiducial indicia 530. e.g., markers, may exist on one or both jaws 510 to create a reference system or scale for determining the lengths L1, L2, and L3 and angle A. Fiducial indicia 530 of the jaws 510 may be marked so as to create a recognizable contrast when viewed by an imagining device, such as imaging device 490. And although FIGS. 5A and 5B show fiducial indicia 530 as a checkerboard style pattern, other patterns including dots, lines, and/or the like may alternatively be used. Examples of other marker designs, configurations, and tracking are described in commonly-owned U.S. Pat. App. Pub. No. 2010/0168763, filed Apr. 23, 2009 and disclosing "CONFIGURATION MARKER DESIGN AND DETECTION FOR INSTRUMENT TRACKING", the full disclosure of which is included herein by reference.

In some embodiments a force and/or torque magnitude limit is applied when controlling the jaws. The force and/or torque magnitude limit functions as an upper limit of an amount of force and/or torque that may be applied to the jaws to make certain no excessive force and/or torque is applied to the material. In some examples a default force and/or torque magnitude limit is determined such that it is safe for all possible material sizes, shapes, positions, and/or properties of the grasped material being grasped by the jaws. In some embodiments, the default force and/or torque magnitude limit is determined such that it prevents splaying of the jaws when the material is grasped closer to the proximal end of the jaws rather than the distal end of the jaws. In some embodiments, the default force and/or torque magnitude limit is determined such that the grasping of the jaws is safe for a material grasped closer to the proximal end of the jaws rather than the distal end of the jaws, and therefore the default force and/or torque magnitude limit may prevent exerting a sufficient force and/or torque on the material when the material is grasped at the distal end of the jaws. Thus, the default force and/or torque magnitude limit may be unduly limiting for grasping scenarios with some material sizes, shapes, positions, and/or properties. In some examples, the default force and/or torque magnitude limit depends on parameters such as a material type, a procedure to be performed on the material, a position and/or orientation of the instrument or end effector, and/or the like.

Returning back to FIGS. 5A and 5B, in some embodiments, the force and/or torque magnitude limit "T" is determined based on one or more of the length L1, L2, L3, angle A, and/or the like. In some examples, the force and/or torque magnitude limit T that is applied to the jaws 510 is determined based on a first function F1 of one or more of the lengths L1, L2, and L3, e.g., T=F1 (L1, L2, L3). In some examples, the force and/or torque magnitude limit T applied to jaws 510 is determined as a second function F2 of one or more of the lengths L1, L2, and L3, and/or the angle A, e.g., T=F2 (L1, L2, L3, A). In some embodiments, the functions F1 and F2 are empirically determined such that a required torque limit T is determined based on the lengths L1, L2, and L3 and/or the angle A and the determined values along with the lengths and the angle are saved as lookup tables in memory for reference. In some embodiments, the functions F1 and F2 additionally depend on "other parameters" such as a procedure to be performed on the material, a material type, other size and/or shape information, an operator preference, a position and/or orientation of the instrument or end effector, and/or the like and therefore a number of lookup tables are composed based on the other parameters and are stored in memory. In some examples, the functions F1 and F2 are one of a linear function or a non-linear function.

Figure 6:
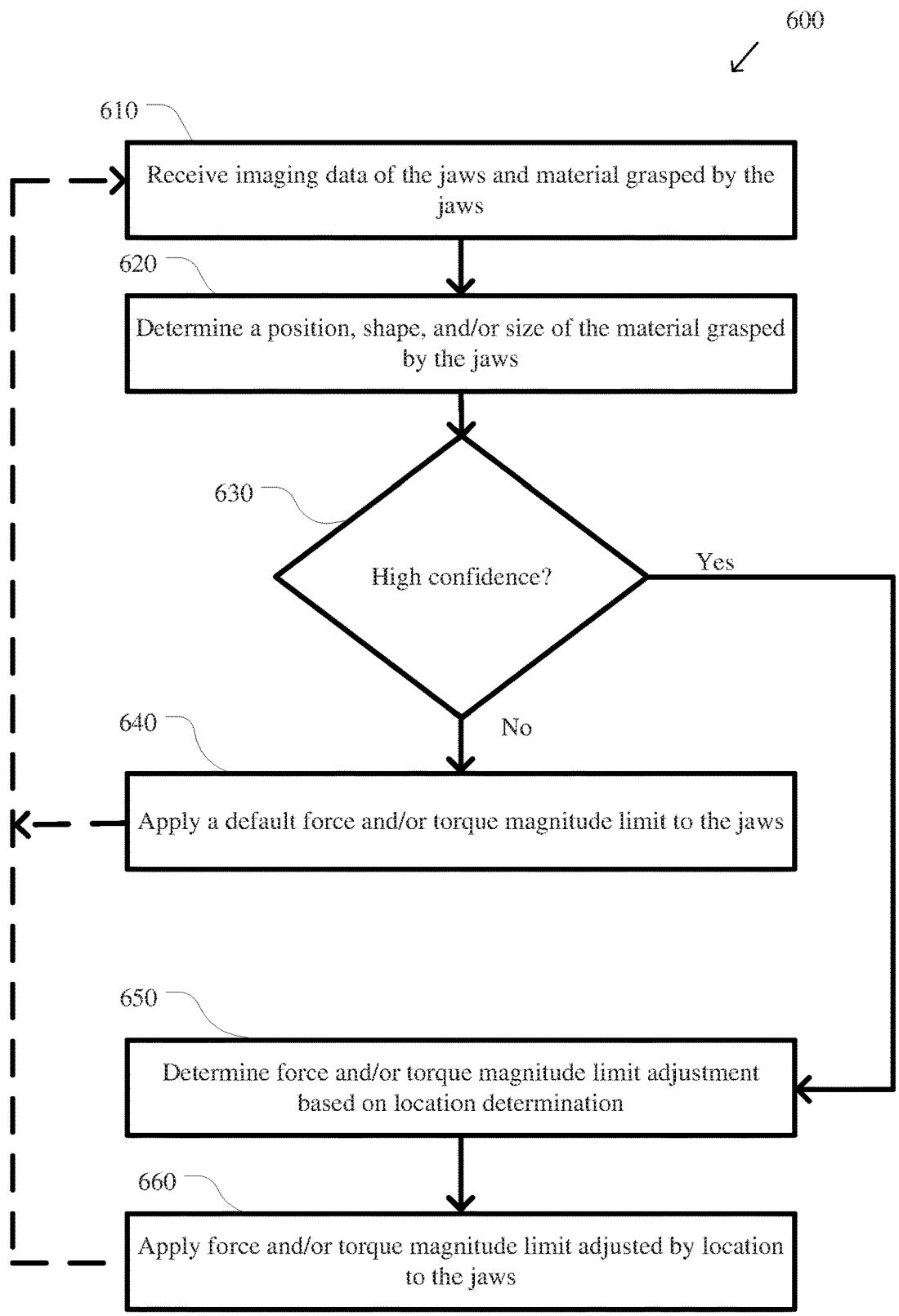
FIG. 6 is a simplified diagram of a method of force and/or torque magnitude limit adjustment, according to some embodiments.

FIG. 6 is a simplified diagram of a method 600 of force and/or torque magnitude limit adjustment, according to some embodiments. One or more of the processes 610-660 of method 600 may be implemented, at least in part, in the form of executable code stored on non-transient, tangible, machine readable media that when run by one or more processors (e.g., the processor 160 in control unit 150) may cause the one or more processors to perform one or more of the processes 610-660. In some embodiments, method 600 may be performed by one or more applications, such as control module 180 and/or image processing module 190. In some embodiments, method 600 may be used to adjust the force and/or torque magnitude limit of an instrument, such as instrument 200. In some examples, the adjusted force and/or torque magnitude limit may correspond to a maximum force and/or torque magnitude that can be applied to grasping jaws, such as jaws 310, a maximum force and/or torque magnitude that can applied by one or more drive mechanisms of the grasping jaws, such as drive mechanisms 250, and/or the like. In some embodiments, the adjusted force and/or torque magnitude limit may be applied to control algorithms for motors, solenoids, servos, active actuators, hydraulic actuators, pneumatic actuators, and/or the like.

In some examples, the force and/or torque magnitude limit adjustment may be activated and/or deactivated by an operator of the instrument. e.g., an operator, and/or may be activated and/or deactivated by a control application, such as control module 180. In some examples, a display screen (not shown) may be coupled to the control unit 150 of FIG. 1 and the received imaging data from the imaging device may be displayed on the display screen. In some examples, an indication of whether force and/or torque magnitude limit adjustment is activated and/or deactivated may be displayed on the display screen for the operator or rendered as an audio signal, haptic signal or other feedback signals to the operator. When force and/or torque magnitude limit adjustment is not activated, a predetermined default force and/or torque magnitude limit, described below, may be applied to the material. In some embodiments, the default force and/or torque magnitude limit is determined based on an assumption that the grasped material is located near the distal end of the jaws.

At a process 610, imaging data of the jaws and the material grasped by the jaws are received. In some examples, the imaging data may be received by an imaging device consistent with the imaging device 490 of FIG. 4 and the received imaging data may be received from a worksite consistent with the worksite 400 of FIG. 4. In some examples, an operator may manipulate one or more master controls of an operator console, such as one or more master manipulators, levers, pedals, switches, keys, knobs, triggers, and/or the like, to teleoperate an articulated arm, such as one of the articulated arms 120 of FIG. 1, to which an instrument having jaws, such as the jaws 410, within the worksite 400. In some examples, the operator may manipulate one or more master controls of an operator console to teleoperate another articulated arm 120 that includes the imaging device 490 such that the imaging device is placed at position that may image the worksite 400. In some examples, the received imaging data from the imaging device may be consistent with imaging data 500 and/or 570 of FIGS. 5A and 5B.

At a process 620, a position, shape, and/or size of the material grasped by the jaws is determined. In some embodiments, a received imaging data is processed and the jaws and the material grasped by the jaws are recognized in the received imaging data. In some examples, the position of the material is determined relative to the jaws, for example relative to where the jaws are joined together at the proximal end of the jaws, or relative to the distal end of the jaws. Also, determining the position, shape, and/or size may include determining one or more of the lengths L1, L2, L3 and/or the angle A. In some examples, as shown in FIGS. 5A and 5B, the jaws may include fiducial indicia and/or markers such that the lengths L1, L2, L3 are determined by using the markers. In some examples, when the jaws and the material grasped by the jaws are recognized, a score or a confidence factor is corresponding to the recognition is determined. The score or the confidence factor may be an indication of how reliable the recognition is. The process 620 is described in more details with respect to FIG. 7. In some examples, the score or the confidence factor is a measure of confidence in the recognition process where a higher score or confidence factor provides higher confidence in the recognition process.

At the process 630, it is determined whether the position, shape, and/or size of the grasped material is determined with high confidence (e.g., with a score or confidence factor above a predetermined threshold). As described with regards to process 620, the score or the confidence factor corresponding to the recognition may be used as an indication of the reliability of the recognition process. If the recognition process has a score or a confidence factor below the predetermined threshold, e.g., below a percent in the range of 60 to 90 percent, then the position, shape, and/or size of the grasped material may not be determined with sufficient confidence to justify a force and/or torque magnitude limit adjustment. In some examples, when the score or the confidence factor is below a predetermined threshold because of, for example, too much of the jaws are occluded, limited field of view, incorrect viewing angle, limited lighting, and/or other imaging issues, the recognition process or the recognized objects may not be sufficiently reliable to justify a force and/or torque magnitude limit adjustment. Alternatively, when the recognition process has a score or a confidence factor above or equal to the predetermined threshold, then the position, shape, and/or size of the grasped material may be determined with sufficient confidence to justify a force and/or torque magnitude limit adjustment. The predetermined threshold of the score or confidence factor can be determined empirically during a training period. The predetermined threshold may additionally be adjusted based on operator preference. Therefore, process 630 may use the score or the confidence factor determined by process 620 to determine whether the position, shape, and/or size is determined with confidence. When the position, shape, and/or size is determined with confidence, a force and/or torque magnitude limit for the actuation applied to the jaws may be determined using a process 650. When the position, shape, and/or size is not determined with confidence, the force and/or torque magnitude limit of the actuation applied to the jaws may be set to a default value using a process 640.

At the process 640, a default force and/or torque magnitude limit is applied to the jaws. In some examples, the recognition of the jaws and the grasped material by the jaws is not determined with sufficient confidence (e.g., when the score or the confidence factor of the recognition is below the predetermined threshold) and the default force and/or torque magnitude limit is applied to the jaws. Also, the default force and/or torque magnitude limit may comprise a default upper force and/or torque magnitude limit and a default lower force and/or torque magnitude limit and thus applying the default force and/or torque magnitude limit to the jaws may include applying the default upper and lower force and/or torque magnitude limits. In some examples, the default torque limit is initially applied to the jaws and the process 640 retains the default torque limit.

In some embodiments, the force and/or torque magnitude limit adjustment is deactivated as a safety measure by the operator of the instrument to prevent applying forces and/or torques that may damage the material and/or the jaws and thus a default force and/or torque magnitude limit is applied to the jaws. In some embodiments, the default force and/or torque magnitude limit is selectable by the operator of the instrument based on a material type, a procedure to be performed on the material, a position and/or orientation of the instrument or end effector, and/or the like.

At a process 650, an adjusted force and/or torque magnitude limit is determined based on the determined position, shape, and/or size of the material grasped between the jaws. In some embodiments, the adjusted force and/or torque magnitude limit is applied to alter an initially applied default force and/or torque magnitude limit. In some examples, the force and/or torque magnitude limit may be determined as a function F1 or F2 of one or more of the lengths L1, L2, L3, and/or A as described with respect to FIGS. 4, 5A, and 5B. In some examples, instead of determining the force and/or torque magnitude limit, a force and/or torque magnitude limit adjustment to the default force and/or torque magnitude limit is determined based the position, size, and/or shape of the grasped material and using one or more functions of one or more of the lengths L1, L2, and L3, and/or the angle A.

In some examples, the force and/or torque magnitude limit adjustment may be performed using lookup tables that can be retrieved from memory such as memory 170 of FIG. 1. The lookup tables may include entries that include calculated force and/or torque magnitude limits and/or calculated force and/or torque magnitude limit adjustments based on one or more of the lengths L1, L2, L3, and/or angle A. In some examples, other parameters that may include one or of a procedure to be performed on the material, a material type, a position and/or orientation of the instrument or end effector, and/or the like, may also be incorporated into the lookup tables In some embodiments, the outcome of the functions F1 and F2 may numerically be calculated based on the sampled parameters of the functions and the outcome may be saved as lookup tables in the memory. The lookup tables may be used to determine the force and/or torque magnitude limit or a corresponding force and/or torque magnitude limit and/or and an adjustment to force and/or torque magnitude limit based on the parameters. Also, interpolation and/or curve fitting can be used to determine an amount of force and/or torque magnitude limit or an amount of force and/or torque magnitude limit adjustment between entries in the lookup tables. In some examples, the interpolation and/or curve fitting may include linear interpolation, polynomial interpolation, cubic spline modeling, and/or the like.

In some embodiments, adjusting the force and/or torque magnitude limit includes adjusting a lower force and/or torque magnitude limit and an upper force and/or torque magnitude limit. In some examples, the upper force and/or torque magnitude limit adjustment and the lower force and/or torque magnitude limit adjustment depend on the position, size, and/or shape of the grasped material relative to the jaws and are calculated based on functions of one or more of the lengths L1, L2, and L3, and/or the angle A. In some examples, instead of an upper and lower force and/or torque magnitude limits, a range of acceptable force and/or torque magnitudes is defined during force and/or torque magnitude limit adjustment. As noted, the upper and lower force and/or torque magnitude limits may depend on a material type, a procedure to be performed on the material, a position and/or orientation of the instrument or end effector, and/or the like.

At a process 660, the force and/or torque magnitude limit adjustment based on the position, size, and/or shape of the material is applied to the jaws. In some examples, the force and/or torque magnitude limit adjustment may be applied as a force and/or torque magnitude limit on the one or more actuators used to operate the jaws. As noted above, initially a default force and/or torque magnitude limit may be applied. Then if it is determined that the position, size, and/or shape of the grasped material is determined with confidence, an adjustment to the default force and/or torque magnitude limit may be applied. The adjustment may be determined based on a total distance from the proximal end of the jaws to the effective point of exerting the force on the material or may be determined based on functions F1 or F2 of one or more of the lengths L1, L2, and L3, and/or the angle A. In some examples, the force and/or torque magnitude limit adjustment is applied to both the lower and upper jaws. Also, in some embodiments, one of the jaws is fixed and thus the force and/or torque magnitude limit adjustment is applied to one of the jaws. For example, the, the lower jaw is fixed and the force and/or torque magnitude limit adjustment is applied to the upper jaw.

Also, the default force and/or torque magnitude limit or an adjustment to the default force and/or torque magnitude limit may be applied using a limit on a parameter such as a current of the drive component, a drive mechanism, a drive unit, and/or an actuator such as a motor, solenoid, servo, active actuator, or a pressure limit of a hydraulic actuator, a pneumatic actuator, and/or the like. After the adjusted force and/or torque magnitude limit or the default force and/or torque magnitude limit is applied during processes 660 and/or 640, respectively, the force and/or torque magnitude limit adjustment process may be optionally repeated by returning to process 610.

Figure 7:
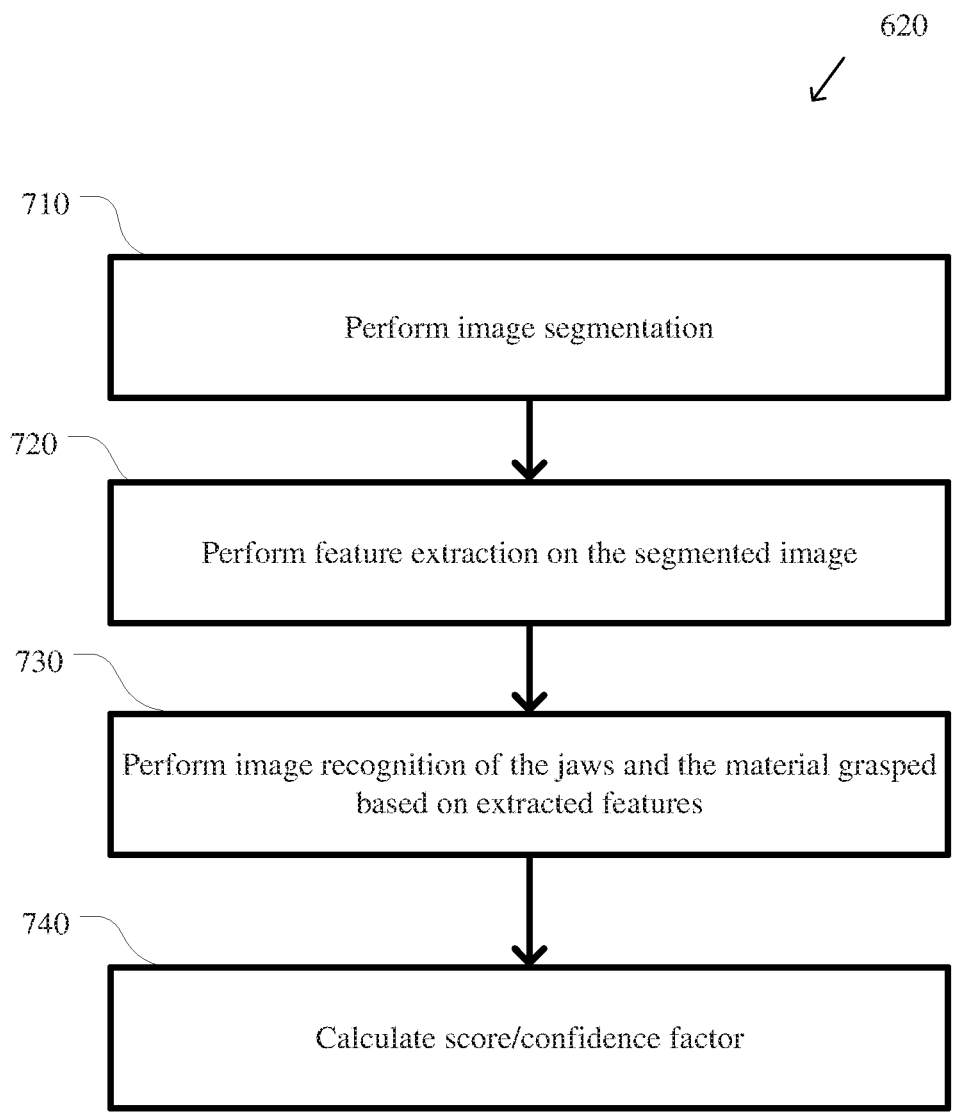
FIG. 7 is a simplified diagram of a method of image recognition, according to some embodiments.

FIG. 7 is a simplified diagram of process 620 according to some embodiments. One or more of the processes 710-740 of process 620 may be implemented, at least in part, in the form of executable code stored on non-transient, tangible, machine readable media that when run by one or more processors (e.g., the processor 160 in control unit 150) may cause the one or more processors to perform one or more of the processes 710-740. In some embodiments, process 620 may be performed by one or more applications, such as image processing module 190 of FIG. 1. In some examples, the processes 710-740 may be implemented by respective modules of an image processing unit that may be executed by the image processing module 190. In some embodiments, process 620 may be used to recognize the jaws and a grasped material in the imaging data of a worksite, such as shown in FIGS. 5A and 5B, and to determine, with respect to the jaws, a position, size, and/or shape of the grasped material by the jaws as shown by process 620 of FIG. 6.

At a process 710, image segmentation may be performed. In some examples, the image segmentation may be performed by a segmentation module such a as segmentation module of the image processing module 190 of FIG. 1. The image segmentation is performed on the received imaging data. The imaging data may be received by an imaging device consistent with the imaging device 490 of FIG. 4 from a worksite consistent with the worksite 400 of FIG. 4.

In some examples, the segmentation module may partition the imaging data into a set of multiple segments such that each segment includes a group of data points (e.g., pixels) having shared characteristics; such that the set of multiple segments cover the entire imaging data. In some examples, shared characteristics may include one or more of similar brightness, similar texture such as edge texture, similar color, and/or the like. Image segmentation may create a segmented imaging data corresponding the received imaging data. In some examples, the image segmentation module may separate the material and the jaws into separate segments.

In some embodiments, the segmentation module may include an edge detection module (e.g., an edge detector) to perform one or more edge detection operations at one or more directions or a combination thereof on the imaging data as part of the segmentation process such that by emphasizing the boundaries of the objects and/or regions present in the imaging data, make the objects and/or regions more distinct from each other. In some examples, one or more of the edge detection operators known to one of ordinary skill in the art of image processing, such as Sobel, Roberts, Canny, Laplacian of Gaussian, and/or the like, may be applied to the imaging data. In some examples, a customized edge detection operator of a predefined size may be applied to the imaging data to enhance discontinuities, e.g., edges, in one or more directions such as zero degrees, 45 degrees, 90 degrees, and 135 degrees in the imaging data. The customized edge detection operator can be a factored combination of two or more of the above mentioned edge detection operators. In some embodiments, a threshold operator may be applied to data points of the imaging data after applying the edge detection operation to determine whether data point is an edge pixel. In some examples, the threshold operator may have hysteresis and determines a data point to be an edge pixel based on its own value and the neighboring data point values to maintain a continuity of edge pixels in one or more directions.

In some embodiments, the segmentation module may include a blob detection module to perform one or more blob detection operations on the imaging data as part of the segmentation process such that a set of image regions that have similar characteristics such as brightness, texture, or color, may be distinguished from the surrounding regions. In some examples, one or more of the blob detection operators known to one of ordinary skill in the art of image processing, such as Laplacian of Gaussian of different sizes, Difference of Gaussian of different sizes, Hessian of different sizes, and/or the like, may be applied to the imaging data. In some examples, a customized blob detection operator of different scales may be applied to the imaging data. The customized blob detection operator may be a factored combination of two or more of the above mentioned blob detection operators.

In some embodiments, the segmentation module may include a morphological filter module to perform one or more morphological filtering operations on the imaging data as part of the segmentation process. In some examples, one or more of the morphological operators known to one of ordinary skill in the art of image processing, such as Dilation, Erosion, and/or a combination of Dilation and Erosion such as Opening, Closing, etc., may be applied to the imaging data. In some examples, a customized morphological operator using a combination of morphological operations and implementing morphological structures of predefined sizes and shapes may be applied to the imaging data. The morphological structures may have a size of 3 to 20 pixels, e.g., 5 pixels, in each dimension. The customized morphological operator may be a factored sequence of two or more of the above mentioned morphological operators. The morphological filtering may be performed after the edge detection process to enhance the edges or after the blob detection process to smooth the image regions. Alternatively, two or more morphological filtering using structuring elements of different sizes may be implemented sequentially to perform blob detection or edge detection.

In some embodiments, the imaging device, may generate color imaging data and the above described operations may be performed on one or all primary colors of the imaging data and the color information may be used for enhancing the segmentation operation. In some examples, the determination that a data point is an edge pixel can be determined by considering the data point in more than one primary color. In some examples the imaging device may acquire the imaging data in one or more portions of the spectrum (e.g., infrared, ultraviolet, and/or the like). In some examples, the imaging device may generate stereoscopic views of the worksite of interest using the two lenses and may use depth information of the jaws and the material grasped by the jaws in the stereoscopic image when setting the torque adjustment.

Alternatively, in some embodiments, the imaging device may generate color imaging data and the segmentation process may be performed based on one or more of intensity/brightness and/or hue of the color imaging data. In some examples, the imaging data may be segmented in the intensity space, in the hue space, or both. In some examples, when the imaging data is segmented in both intensity and hue spaces, then the segmented imaging data in the two spaces may be combined to reach a single segmented imaging data. In some examples, the segmentation module may receive the imaging data and may generate the segmented imaging data as the output of the segmentation module corresponding the received imaging data. In some examples, the segmentation module may receive imaging data obtained from a worksite of interest generated by the imaging device 490 of FIG. 4. The obtained imaging data may include features similar to the features of imaging data 500 and/or 570 of FIGS. 5A and 5B, such as images of jaws, fiducial indicia, grasped material, background elements of a worksite, and/or the like.

At a process 720, feature extraction may be performed. In some examples, the feature extraction may be performed by a feature extraction module, such as a feature extraction module of the image processing module 190 of FIG. 1. The feature extraction is performed on segmented imaging data generated by the segmentation process 710 and may generate the features and/or information of the features such as a shape, a size, a position, an orientation and/or the like of the features, and/or the like.

In some examples, the feature extraction depends on the one or more objects that are intended, e.g., predetermined, to be recognized in the imaging data. For example, FIGS. 4, 5A, and 5B may be processed to find the jaws and the material grasped by the jaws and thus the features may be related to the jaws and the material. In some examples, the feature extraction process may remove background objects to reduce the complexity of the imaging data and keep the features that are related to recognizing the intended objects, e.g., the jaws and the material. In some examples, the features may include parallel lines, e.g., edges, of the rectangular shape jaws, sharp corners (of the jaws), fiducial indicia on the jaws, where the jaws pivot relative to each other, and/or the like. Thus, the feature extraction module may use the outcome of the edge detection and blob detection modules of the segmentation module to extract the features and to determine information of the features such as positions of the features in the imaging data, sizes of the features, shapes of the features, and/or the like.

In some examples, the feature extraction may be performed on the received imaging data instead of the segmented imaging data such that process 710 is optional and may be omitted. The feature extraction module may use the imaging data received by the imaging device and may use correlation (e.g., normalized correlation) to find the features. In some examples, the feature extraction module may use normalized correlation to find intended features corresponding to the intended objects such as one of the jaws, both jaws, or the material, in the received imaging data. In some examples, normalized correlation may return a matching score indicating how good a match has been found for the feature and may also indicate a position, size, and/or shape of the feature in the imaging date. In some examples, the feature extraction module may access a database in a memory, e.g., memory 170 of the control unit 150 of FIG. 1, that includes a lookup table of intended features and then for each feature may perform normalized correlation on all elements of the lookup table of features to find the best match based on the matching score of the normalized correlation.

As described above, normalized correlation may be used to find the matching features in the received imaging data by performing the normalized correlation on elements of a lookup table that includes a list of intended features such as the two jaws and the material, the features having different orientations and viewed from different distances and viewing angles. Then the scores or confidence factors of the normalized correlations are compared with a predetermined value to generate acceptable features, or to determine the best matches of each feature.

At a process 730, image recognition of the jaws and the grasped material may be performed based on the extracted features. In some examples, the image recognition may be performed by a recognition module, such as a recognition module of the image processing module 190 of FIG. 1. The image recognition may be performed on the extracted features generated by the feature extraction process 720 and may generate the recognized patterns or objects that may include a pair of jaws with a material grasped between the jaws.

In some embodiments, the recognition module may include a statistical recognition module. In some examples, the features may be defined as the jaws, the material, and an angle between the jaws. For each feature, a mean value and an acceptable range may be determined. For example, each jaw may have a mean length, width, and/or area and an acceptable range of variations in length, width, and/or area. The material may have a mean area and/or an acceptable range of variation of the area. Similarly, the angle between the jaws may have a mean value and/or an acceptable variation. In some examples, the mean and/or the acceptable range of a feature may be considered as a probability distribution of the feature such that the probability is the highest when the feature is at its mean value and the probability gets smaller as it gets further away from the mean and approaching zero at the ends of the acceptable range. In some embodiments, the statistical recognition module may declare a match (e.g., indicating the jaws and the grasped material are found) when the above indicated features are recognized and are within the acceptable ranges. In some examples, a score and/or a confidence factor is calculated based on the probability that the features are found within the acceptable range of the features. In some examples, the recognition module may also recognize one or more of the lengths L1, L2, and L3 and/or the angle A as defined above. The recognized objects may further include a recognized pattern of fiducial indicia on the jaws 510. In some examples, a measure of the recognized lengths L1, L2, and L3 and/or the angle A may also be determined using the recognized fiducial indicia on the jaws 510. In some examples, if the fiducial indicia on the jaws are not detectable, the lengths L1, L2, and L3 and/or the angle A may not be confidently determined.

In some examples, the segmentation module and/or the feature extraction module are optional and the recognition of the jaws and the grasped material may be performed on the received imaging data instead of the extracted features such that processes 710 and 720 may be omitted. In some embodiments, recognition module may have access to and may retrieve a database in a memory (e.g., memory 170 of the control unit 150 of FIG. 1) that includes a lookup table of anticipated objects/patterns that comprises the jaws and/or a grasped material between the jaws, having different orientations and/or acquired from different viewing angles and/or viewing distances. In some embodiments, the recognition module may directly use the imaging data received by the imaging device and/or may use correlation (e.g., normalized correlation) to find the object/pattern of the jaws and/or the grasped material between the jaws in the received imaging data. In some examples, normalized correlation may return a matching score indicating how good a match has been found. In some examples, the recognition module may perform normalized correlation on all elements of a lookup table to generate the scores and/or confidence factors of the normalized correlations between the received imaging data and the elements of the lookup table and then to determine acceptable scores and/or confidence factors. In some examples, the scores and/or confidence factors are compared to find the highest score and/or confidence factor corresponding to the object that is best matched to the received imaging data.

In some embodiments, the recognition module may include a structural recognition module. The structural recognition module may assume that the patterns or objects to be recognized are ordered sequences of features like in a sentence and thus may have a grammar. Therefore, in addition to determining whether each of the expected features are found in a imaging data, it may be determined whether the features also satisfy a grammar of how the features should be positioned relative to each other and how the features should be related. For example, if the jaws and the material are found but the material is not between the jaws, the pattern is not found and the score and/or confidence factor may be set to zero and/or correspondingly low. In some examples, a probability may be assigned to each feature and additionally another probability may be assigned to the relation between the features and how the features are related to each other and as described below a total score and/or confidence factor may be found when an object/pattern is recognized. In some examples, the feature extraction module may extract, from the imaging data, features that include two jaws, having a length and width in the acceptable range, and a material between the two jaws. However, the recognized jaws may not be pivoted at the proximal end of the two jaws and thus the grammar of how the features should be located relative to each other may not be satisfied. As a result, the structural recognition module does not recognize the recognized features, in the imaging data as an acceptable object/pattern and the score and/or confidence factor may be set to zero and/or correspondingly low.

At a process 740, a score or confidence factor determination may be performed based on the recognized object or patterns. The score and/or confidence determination may also be performed by a score and/or confidence factor module of the image processing module 190 of FIG. 1. The score and/or confidence factor may be determined based on information associated with the recognized patterns such as the scores or confidence factors of the features of the pattern. Alternatively, when the processes 710 and 720 are skipped and correlation, such as normalized correlation is performed on the received imaging data, the score or confidence factor may be determined as the score or confidence factor of the best match.

In some examples, the score and/or confidence factor module receives the recognized patterns and/or a probability associated with the recognized patterns at its input and generates a recognition score value and/or a recognition confidence factor at its output. In some examples, a score and/or a confidence factor is calculated based on the probability of the features being present and detected. In some examples, the score and/or confidence factor is calculated by multiplying the probabilities of the features, by a weighted sum of the probabilities of the features, or a combination thereof. In some examples, such as when using the structural recognition module, a probability may be assigned to each feature and additionally another weight may be assigned to the relation between the features and similarly a score and/or confidence factor may be calculated when a match is found. In some examples, the calculated score and/or confidence factor may be multiplied by a fixed factor, e.g., 1000, to normalize the score/confidence factor between zero and a 1000. In some examples, if at least one of the features are outside the acceptable range or a grammar rule is violated, then the score and/or confidence factor is zero or correspondingly low and no match is found. In some examples, when the features are outside the acceptable range and/or a grammar rule is violated, the score and/or confidence factor may not be set to zero but instead may be penalized by reducing the score and/or confidence factor by a predefined amount or multiplying the score and/or confidence factor by a predefined coefficient less than one.

As described, when the recognition module directly implements the recognition on the imaging data received by the imaging device and uses correlation, such as normalized correlation, for object/pattern recognition, the matching score of the normalized correlation, multiplied by 1000, may be assigned as the score and/or confidence factor.

Some examples of control units, such as control unit 150 may include non-transient, tangible, machine readable media that include executable code that when run by one or more processors (e.g., processor 160) may cause the one or more processors to perform the processes of methods 600 and 620. Some common forms of machine readable media that may include the processes of methods 600 and 620 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device, the device comprising:
   an image processing unit configured to:
      receive imaging data of a two-jawed end effector supported by the device; and
      process the imaging data to recognize the two-jawed end effector and a material grasped by the two-jawed end effector;
   wherein the device is configured to:
      adjust a force magnitude limit or a torque magnitude limit used to limit actuation of the two-jawed end effector based on the received imaging data.

2. The device of claim 1, wherein the image processing unit is further configured to determine one or more of a position, an orientation, a size, or a shape of the material based on the received imaging data.

3. The device of claim 1, wherein:
   at least one jaw of the two jawed end effector includes fiducial indicia;
   the image processing unit is configured to recognize the fiducial indicia in the received imaging data; and
   the image processing unit is configured to determine one or more of a position, an orientation, a size, or a shape of the material based at least on the fiducial indicia.

4. The device of claim 1, wherein the image processing unit is further configured to determine a confidence level to which a position, an orientation, a size, or a shape of the grasped material relative to the two jawed end effector is determined.

5. The device of claim 4, wherein the device is further configured to:
   compare the confidence level to a predetermined threshold; and
   apply a default force magnitude limit or a default torque magnitude limit used to limit actuation of the two-jawed end effector in response to the confidence level being below the predetermined threshold.

6. The device of claim 1, wherein the image processing unit is further configured to:
   determine, based on the processed imaging data, a position of a proximal end of jaws of the two jawed end effector where the jaws pivot relative to each other;
   determine, based on the processed imaging data, a position of at least one distal end of at least one jaw; and
   determine, based on the processed imaging data, a position of a grasping zone, wherein the grasping zone is where the at least one jaw and the grasped material are in contact.

7. The device of claim 1, wherein the image processing unit is further configured to:
   determine, based on the processed imaging data, one or more of:
      a first length between a proximal end of jaws of the two-jawed end effector and a proximal end of a grasping zone, wherein the grasping zone is where at least one jaw and the grasped material are in contact;
      a second length corresponding to a length of the grasping zone;
      a third length between a distal end of the grasping zone and the distal end of the at least one jaw; and
      an angle between the jaws of the two-jawed end effector.

8. The device of claim 7, wherein the device is further configured to adjust the force magnitude limit or the torque magnitude limit based at least on a function of one or more parameters the first length, the second length, the third length, and the angle.

9. A method of operating a computer-assisted device, the method comprising:
   receiving, by an image processing unit executing on one or more processors, imaging data of a two jawed end effector;
   processing the imaging data to recognize the two jawed end effector and a material grasped by the two jawed end effector;
   determining a position, an orientation, a size, or a shape of the material relative to the two jawed end effector;
   determining whether the position, the orientation, the size, or the shape is determined with confidence; and
   adjusting, when the position, the size, or the shape determination is with confidence, a force magnitude limit or a torque magnitude limit used to limit actuation of the two jawed end effector or applying, when the position determination is without confidence, a default force magnitude limit or a default torque magnitude limit used to limit actuation of the two jawed end effector.

10. The method of claim 9, wherein:
    at least one jaw of the two jawed end effector includes fiducial indicia; and
    the method further comprises:
       recognizing the fiducial indicia in the received imaging data; and
       determining one or more of the position, an orientation, the size, or the shape of the material based at least on the fiducial indicia.

11. The method of claim 9, further comprising:
determining a confidence level to which the position, the size, or the shape of the grasped material relative to the two-jawed end effector is determined;
comparing the confidence level to a predetermined threshold; and
applying a default force magnitude limit or a default torque magnitude limit to limit the actuation of the two-jawed end effector in response to the confidence level being below the predetermined threshold.

12. The method of claim 9, further comprising:
determining, based on the processed imaging data, a position of a proximal end of jaws of the two jawed end effector where the jaws pivot relative to each other;
determining, based on the processed imaging data, a position of at least one distal end of at least one jaw; and
determining, based on the processed imaging data, a position of a grasping zone, wherein the grasping zone is where the at least one jaw and the grasped material are in contact.

13. The method of claim 9, further comprising:
determining, based on the processed imaging data, one or more of:
a first length between a proximal end of jaws of the two-jawed end effector and a proximal end of a grasping zone, wherein the grasping zone is where at least one jaw and the grasped material are in contact;
a second length corresponding to a length of the grasping zone;
a third length between a distal end of the grasping zone and the distal end of the at least one jaw; and
an angle between the jaws of the two-jawed end effector.

14. The method of claim 13, further comprising adjusting the force magnitude limit or the torque magnitude limit based at least on a function of one or more parameters the first length, the second length, the third length, and the angle.

15. A non-transitory machine-readable medium having stored thereon machine-readable instructions executable to cause a machine to perform a method comprising:
receiving, by an image processing unit executing on one or more processors, imaging data of a two jawed end effector;
processing the imaging data to recognize the two jawed end effector and a material grasped by the two jawed end effector;
determining a position, an orientation, a size, or a shape of the material relative to the two jawed end effector;
determining whether the position, the orientation, the size, or the shape is determined with confidence; and
adjusting, when the position, the size, or the shape determination is with confidence, a force magnitude limit or a torque magnitude limit used to limit actuation of the two jawed end effector or applying, when the position determination is without confidence, a default force magnitude limit or a default torque magnitude limit used to limit actuation of the two jawed end effector.

16. The non-transitory machine-readable medium of claim 15, wherein the method further comprises:
recognizing fiducial indicia in the received imaging data; and
determining one or more of the position, an orientation, the size, or the shape of the material based at least on the fiducial indicia.

17. The non-transitory machine-readable medium of claim 15, wherein the method further comprises:
determining a confidence level to which the position, the size, or the shape of the grasped material relative to the two-jawed end effector is determined;
comparing the confidence level to a predetermined threshold; and
applying a default force magnitude limit or a default torque magnitude limit to limit the actuation of the two-jawed end effector in response to the confidence level being below the predetermined threshold.

18. The non-transitory machine-readable medium of claim 15, wherein the method further comprises:
determining, based on the processed imaging data, a position of a proximal end of jaws of the two jawed end effector where the jaws pivot relative to each other;
determining, based on the processed imaging data, a position of at least one distal end of at least one jaw; and
determining, based on the processed imaging data, a position of a grasping zone, wherein the grasping zone is where the at least one jaw and the grasped material are in contact.

19. The non-transitory machine-readable medium of claim 15, wherein the method further comprises:
determining, based on the processed imaging data, one or more of:
a first length between a proximal end of jaws of the two-jawed end effector and a proximal end of a grasping zone, wherein the grasping zone is where at least one jaw and the grasped material are in contact;
a second length corresponding to a length of the grasping zone;
a third length between a distal end of the grasping zone and the distal end of the at least one jaw; and
an angle between the jaws of the two-jawed end effector.

20. The non-transitory machine-readable medium of claim 19, wherein the method further comprises adjusting the force magnitude limit or the torque magnitude limit based at least on a function of one or more parameters the first length, the second length, the third length, and the angle.

* * * * *

UNITED STATES PATENT AND TRADEMARK OFFICE
CERTIFICATE OF CORRECTION

| | |
|---|---|
| PATENT NO. | : 11,523,839 B2 |
| APPLICATION NO. | : 16/366854 |
| DATED | : December 13, 2022 |
| INVENTOR(S) | : Ashley Lynne Wellman, David W. Weir and Matthew A. Wixey |

It is certified that error appears in the above-identified patent and that said Letters Patent is hereby corrected as shown below:

In the Claims

Column 22, Claim 8, Line 38, please insert --selected from a group consisting of-- after parameters;

Column 23, Claim 11, Line 7, please delete "applying a default force magnitude limit or a default" and insert --applying the default force magnitude limit or the default--;

Column 23, Claim 14, Line 37, please insert --selected from a group consisting of-- after parameters;

Column 24, Claim 17, Line 19, please delete "applying a default force magnitude limit or a default" and insert --applying the default force magnitude limit or the default--;

Column 24, Claim 20, Line 52, please insert --selected from a group consisting of-- after parameters.

Signed and Sealed this
Fourteenth Day of February, 2023

Katherine Kelly Vidal
*Director of the United States Patent and Trademark Office*